US012714655B2

(12) United States Patent
Shi

(10) Patent No.: US 12,714,655 B2
(45) Date of Patent: Aug. 25, 2026

(54) WATER-IN-OIL-TYPE EMULSIFIED SUNSCREEN COSMETIC

(71) Applicant: KAO CORPORATION, Tokyo (JP)

(72) Inventor: Jia Shi, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 517 days.

(21) Appl. No.: 17/997,947

(22) PCT Filed: May 13, 2021

(86) PCT No.: PCT/JP2021/018159

§ 371 (c)(1),
(2) Date: Nov. 4, 2022

(87) PCT Pub. No.: WO2021/230310

PCT Pub. Date: Nov. 18, 2021

(65) Prior Publication Data

US 2023/0165763 A1 Jun. 1, 2023

(30) Foreign Application Priority Data

May 14, 2020 (JP) ................................ 2020-085346

(51) Int. Cl.

| | |
|---|---|
| ***A61K 8/06*** | (2006.01) |
| ***A61K 8/27*** | (2006.01) |
| ***A61K 8/29*** | (2006.01) |
| ***A61K 8/31*** | (2006.01) |
| ***A61K 8/891*** | (2006.01) |
| ***A61Q 17/04*** | (2006.01) |

(52) U.S. Cl.

CPC ................ *A61K 8/064* (2013.01); *A61K 8/27* (2013.01); *A61K 8/29* (2013.01); *A61K 8/31* (2013.01); *A61K 8/891* (2013.01); *A61Q 17/04* (2013.01); *A61K 2800/412* (2013.01); *A61K 2800/413* (2013.01); *A61K 2800/612* (2013.01)

(58) Field of Classification Search

CPC ........ A61K 8/064; A61K 8/0241; A61K 8/29; A61K 8/345; A61K 2800/21; A61K 2800/30; A61K 2800/413; A61K 8/025; A61K 8/19; A61K 8/27; A61K 8/89; A61K 2800/412; A61K 2800/522; A61K 2800/621; A61K 2800/623; A61K 2800/87; A61K 8/11; A61K 8/35; A61K 8/42; A61K 8/46; A61K 8/34

See application file for complete search history.

(56) References Cited

U.S. PATENT DOCUMENTS

| | | | | |
|---|---|---|---|---|
| 10,383,811 | B1 * | 8/2019 | Patel | A61K 8/025 |
| 2005/0180931 | A1 | 8/2005 | Oguchi et al. | |
| 2010/0291011 | A1 | 11/2010 | Ikebe et al. | |
| 2012/0328539 | A1 * | 12/2012 | Tamura | C08G 77/14 424/59 |
| 2014/0205552 | A1 | 7/2014 | Fukuhara | |
| 2014/0348765 | A1 | 11/2014 | Sasaki | |
| 2016/0220457 | A1 | 8/2016 | Yamaguchi et al. | |

FOREIGN PATENT DOCUMENTS

| | | | | |
|---|---|---|---|---|
| CN | 101951876 | A | 1/2011 | |
| CN | 102300549 | A | 12/2011 | |
| CN | 104168882 | A | 11/2014 | |
| EP | 2 392 312 | A1 | 12/2011 | |
| EP | 2 559 426 | A2 | 2/2013 | |
| EP | 3087970 | A1 * | 12/2014 | A61K 8/29 |
| EP | 2 918 260 | A1 | 9/2015 | |
| EP | 4 112 126 | A1 | 1/2023 | |
| EP | 4 151 279 | A1 | 3/2023 | |
| JP | 11-236308 | A | 8/1999 | |
| JP | 2000-191490 | A | 7/2000 | |
| JP | 2002-29916 | A | 1/2002 | |
| JP | 2003335649 | A * | 11/2003 | A61K 7/42 |
| JP | 2004-224757 | | 8/2004 | |
| JP | 2005-232092 | | 9/2005 | |
| JP | 2006-265213 | A | 10/2006 | |
| JP | 2013-43875 | A | 3/2013 | |
| JP | 2013-133306 | A | 7/2013 | |
| JP | 2015-124172 | A | 7/2015 | |
| JP | 5792493 | B2 | 10/2015 | |
| JP | 2016-088935 | | 5/2016 | |
| JP | WO2016076202 | A1 * | 5/2016 | A61K 8/06 |
| JP | 2017-155000 | A | 9/2017 | |

(Continued)

OTHER PUBLICATIONS

Machine translation of Hiroyuki et al., JP2002029916A [online]. Espacenet [retrieved on Feb. 4, 2025]. Retrieved from the internet: <https://worldwide.espacenet.com/patent/>. (Year: 2002).*
JP2003335649A (Year: 2003).*
WO2016076202A1 translation (Year: 2016).*
Extended European Search Report issued Apr. 17, 2024 in European Patent Application No. 21804700.9, 12 pages.
Lem, T. et al., "Selecting the perfect silicone for you formulation," Personal Care, Jul. 2014, XP093147603, pp. 45-48.
International Search Report mailed on Jul. 13, 2021 in PCT/JP2021/018159 filed on May 13, 2021 (2 pages).

(Continued)

*Primary Examiner* — Audrea B Coniglio

(74) *Attorney, Agent, or Firm* — Oblon, McClelland, Maier & Neustadt, L.L.P.

(57) ABSTRACT

A water-in-oil emulsified sunscreen cosmetic including the following components (A1), (A2), (B), and (C), with a content of (D) a non-volatile silicone oil being 0.1 mass % or more and 4 mass % or less, (A1) 5 mass % or more of a hydrophobized titanium dioxide fine particle, (A2) 10 mass % or more of a hydrophobized zinc oxide fine particle, (B) a divalent polyol, and (C) 2 mass % or more and 14 mass % or less of a non-volatile hydrocarbon oil, wherein each mass % is with respect to 100 mass % of the water-in-oil emulsified sunscreen cosmetic.

19 Claims, 1 Drawing Sheet

(56) References Cited

FOREIGN PATENT DOCUMENTS

| | | | |
|---|---|---|---|
| JP | 2019-137679 | A | 8/2019 |
| JP | 2019-156800 | | 9/2019 |
| JP | 2020-200316 | A | 12/2020 |
| JP | 2020-200317 | A | 12/2020 |
| JP | 2020-200318 | A | 12/2020 |

OTHER PUBLICATIONS

"Titanium oxide as a cosmetic raw material", Materials of the Investigative Commission on Measures to Prevent the Health Impairment of Workers Due to Chemical Substances, 2017, 3rd (https://www.mhlw.go.jp/stf/shingi2/0000184629.htm 1), Japan Cosmetic Industry Association (JCIA), (with a partial machine translation).

Hiroshi Fukui, "Designing surface of cosmetic powder", Journal of the Japan Society of Colour Material, vol. 92, No. 11, Nov. 20, 2019 (with a partial machine translation).

* cited by examiner

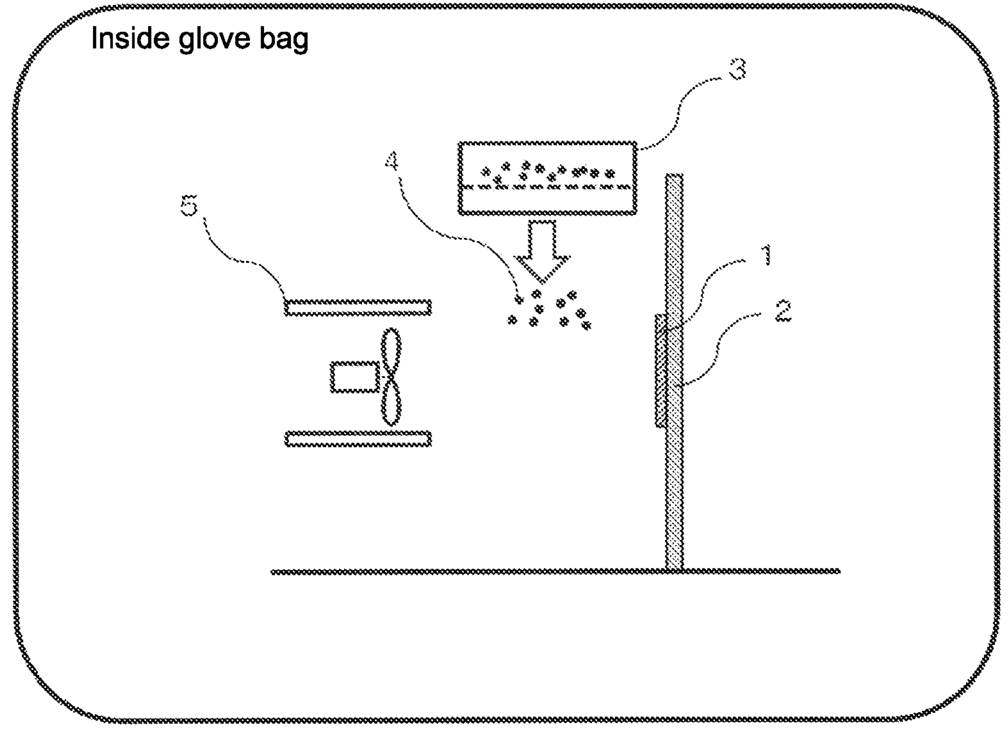
Inside glove bag
3
4
5
1
2

WATER-IN-OIL-TYPE EMULSIFIED SUNSCREEN COSMETIC

CROSS REFERENCE TO RELATED APPLICATIONS

This application is a National Stage entry under 35 U.S.C. § 371 of PCT/JP2021/018159, filed on May 13, 2021, and claims priority to Japanese Patent Application No. 2020-085346, filed on May 14, 2020. The entire contents of both are incorporated herein by reference.

FIELD OF THE INVENTION

The present invention relates to a water-in-oil emulsified sunscreen cosmetic.

BACKGROUND OF THE INVENTION

Sunscreen cosmetics typically contain an ultraviolet absorber and an ultraviolet scattering agent such as titanium dioxide, zinc oxide and the like. Because more gentle cosmetics to the skin have been desired, studies on reducing a content of an organic ultraviolet absorber have been conducted to date. For such cosmetics, for example, ultraviolet shielding cosmetics containing a suspension in which zinc oxide as an ultrafine particle and the like having a specific particle size is dispersed in a silicone-based oil is known (Patent Literature 1).

(Patent Literature 1) JP-A 2000-191490

SUMMARY OF THE INVENTION

The present invention provides a water-in-oil emulsified sunscreen cosmetic, comprising the following components (A1), (A2), (B), and (C), with a content of (D) a non-volatile silicone oil being 0 mass % or more and 5 mass % or less:

(A1) 5 mass % or more of a hydrophobized titanium dioxide fine particle, (A2) 10 mass % or more of a hydrophobized zinc oxide fine particle, (B) a divalent polyol, and (C) 2 mass % or more and 14 mass % or less of a non-volatile hydrocarbon oil.

DETAILED DESCRIPTION OF THE INVENTION

The present inventor has proceeded with the investigation and found that the ultraviolet shielding cosmetic described in Patent Literature 1 had excellent dispersibility in a formulation but, when applied to the skin and dried, the coating film was likely to be uneven, thereby revealing that an ultraviolet protection effect could be insufficient.

Damages to the skin by air hazardous substances can be a cause of atopic dermatitis. For this reason, in recent years demands have grown for suppressing not only the damage by the ultraviolet but also the damage on the skin by air hazardous substances. The investigation by the present inventor found that air hazardous substances less likely adhere to a coating film of a cosmetic when a low content of or no non-volatile silicone oil is used. However, another problem occurred of a use impression of powdery feel when the cosmetic is applied.

The present invention relates to providing a water-in-oil emulsified sunscreen cosmetic which imparts an excellent use impression free from a powdery feel, hardly allows air hazardous substances to adhere to a coating film thereof, and has an excellent ultraviolet protection effect.

The present inventor found that the water-in-oil emulsified sunscreen cosmetic, which contains, in addition to a high content of a hydrophobized titanium dioxide fine particle and a high content of a hydrophobized zinc oxide fine particle, a divalent polyol, a content of 2 mass % or more and 14 mass % or less of a non-volatile hydrocarbon oil, and a content of 0 mass % or more and 5 mass % or less of a non-volatile silicone oil, imparts an excellent use impression free from a powdery feel, but hardly allows air hazardous substances to adhere to a coating film thereof, and has an excellent ultraviolet protection effect. Consequently, the present invention was completed.

The water-in-oil emulsified sunscreen cosmetic of the present invention imparts an excellent use impression free from a powdery feel, hardly allows air hazardous substances to adhere to a coating film thereof, and has an excellent ultraviolet protection effect.

BRIEF DESCRIPTION OF THE DRAWING

FIG. 1 is a schematic drawing showing an evaluation method of the anti-adherence effect on air hazardous substance.

COMPONENTS (A1), (A2)

The water-in-oil emulsified sunscreen cosmetic of the present invention contains (A1) a hydrophobized titanium dioxide fine particle and (A2) a hydrophobized zinc oxide fine particle. The titanium dioxide fine particle and the zinc oxide fine particle can contain trace elements having +2 valent or higher, and metals such as iron, zirconium, calcium, manganese, magnesium, and yttrium can be contained in the titanium dioxide fine particle and the zinc oxide fine particle alone, or in combination of two or more.

The shape of the "hydrophobized titanium dioxide fine particle" and the "hydrophobized zinc oxide fine particle" described above is not particularly limited. Examples thereof include a spherical shape, a plate shape, a bar shape, a spindle shape, a needle shape, and an undefined shape.

The average primary particle size $d_A$ of the "hydrophobized titanium dioxide fine particle" and the "hydrophobized zinc dioxide fine particle" described above is, from a viewpoint of enhancing the ultraviolet protection effect, preferably 1 nm or more, and more preferably 5 nm or more, and preferably 100 nm or less, and more preferably 80 nm or less. From a viewpoint of enhancing the anti-adherence effect on air hazardous substances, it is also preferably 1 nm or more, and more preferably 7 nm or more, and preferably 200 nm or less, more preferably 80 nm or less, and further more preferably 50 nm or less. Specific ranges of the average primary particle size $d_A$ are, from viewpoints of enhancing the ultraviolet protection effect and the anti-adherence effect on air hazardous substances, preferably 1 nm or more and 200 nm or less, more preferably 5 nm or more and 200 nm or less, further more preferably 5 nm or more and 100 nm or less, further more preferably 7 nm or more and 100 nm or less, further more preferably 7 nm or more and 80 nm or less, and particularly preferably 7 nm or more and 50 nm or less.

The average primary particle size $d_A$ in the present description can be determined from an observation image by a transmission electron microscope (TEM). Specifically, an image may be observed by using TEM under a condition of observation magnification of 50 000 times, maximum minor-axes of 300 primary particles in the observation image are measured to calculate the number average value thereof, thereby determining the average primary particle size. The maximum minor-axis herein means, when the "hydrophobized titanium dioxide fine particle" or the "hydrophobized zinc oxide fine particle" has a shape other than a plate shape, the minor axis having the maximum length among the minor axes orthogonal to the major axis. When the "hydrophobized titanium dioxide fine particle" or the "hydrophobized zinc oxide fine particle" has a plate shape, a thickness of 300 primary particles in an observation image observed under the same condition as above is measured to calculate the number average value thereof, thereby determining the average primary particle size.

The components (A1) and (A2) are a hydrophobized titanium dioxide fine particle and a zinc oxide fine particle. The hydrophobization treatment improves the dispersibility of the titanium dioxide fine particle and the zinc oxide fine particle, and enhances the anti-adherence effect on air hazardous substances.

Examples of the hydrophobization treatment include silicone treatment; alkylalkoxysilane treatment; fatty acid treatment; treatment with a fluorine-containing compound such as perfluoroalkyl phosphate ester, perfluoro alcohol, and perfluoroalkylalkoxysilane; treatment with an amino acid such as N-acyl glutamic acid; and alkyl phosphate ester treatment.

Of these, the fatty acid treatment is preferable from viewpoints of increasing the dispersibility and enhancing the ultraviolet protection effect of the component (A1) in the cosmetic. The silicone treatment and alkylalkoxysilane treatment are preferable from viewpoints of increasing the dispersibility and enhancing the ultraviolet protection effect of the component (A2).

Examples of the surface treatment agent used for the fatty acid treatment include a straight-chain or branched-chain fatty acid having 12 or more and 22 or less carbon atoms, or salts thereof. Of these, from viewpoints of increasing the dispersibility and enhancing the anti-adherence effect on air hazardous substances of the component (A1) and the component (A2) in the cosmetic, a straight-chain or branched-chain fatty acid having 14 or more and 22 or less carbon atoms, or salts thereof are preferable, a straight-chain or branched-chain fatty acid having 16 or more and 20 or less carbon atoms, or salts thereof are more preferable, and stearic acid, aluminum stearate, isostearic acid, and aluminum isostearate are further more preferable.

Examples of the surface treatment agent used for the silicone treatment include various silicone oils such as dimethylpolysiloxane, methyl phenyl polysiloxane, methyl hydrogen polysiloxane, methylcyclopolysiloxane, dodecamethylcyclohexasiloxane, tetradecamethylhexasiloxane, a dimethylsiloxane/methyl(polyoxyethylene)siloxane/methyl(p olyoxypropylene)siloxane copolymer, a dimethylsiloxane/methyl(polyoxyethylene)siloxane copolymer, a dimethylsiloxane/methyl(polyoxypropylene)siloxane copolymer, a dimethylsiloxane/methylcetyloxysiloxane copolymer, a dimethylsiloxane/methylstearoxysiloxane copolymer, and an alkyl acrylate/dimethicone copolymer. Of these, from viewpoints of increasing the dispersibility and enhancing the anti-adherence effect on air hazardous substances of the component (A1) and the component (A2) in the cosmetic, methyl hydrogen polysiloxane and dimethylpolysiloxane are preferable.

The surface treatment agent used for the alkylalkoxysilane treatment is preferably alkylalkoxysilane having a straight-chain or branched-chain alkyl group having 6 or more and 20 or less carbon atoms, and more preferably octyltriethoxysilane and octyltrimethoxysilane, from viewpoints of increasing the dispersibility and enhancing the anti-adherence effect on air hazardous substances of the component (A1) and the component (A2) in the cosmetic.

Commercial products of the (A1)hydrophobized titanium dioxide fine particle include MT-100 series, JR series and MPY series manufactured by TAYCA CORPORATION, STR-100 series manufactured by SAKAI CHEMICAL INDUSTRY CO., LTD., and TT055 series, TT051 series and MPT series manufactured by ISHIHARA SANGYO KAISHA, LTD. Commercial products of the (A2) hydrophobized zinc oxide fine particle include MZ-500 series and MZ-300 series manufactured by TAYCA CORPORATION, and FINEX-50 series, FINEX-30 series and FINEX-25 series manufactured by SAKAI CHEMICAL INDUSTRY CO., LTD.

The above-mentioned surface treatment agents can be used alone, or two or more can also be used in combination.

A treatment amount by the surface treatment agent to the entire mass of the component (A1) or the entire mass of the component (A2) is preferably 0.1 mass % or more, and preferably 40 mass % or less, and more preferably 30 mass % or less, from viewpoints of increasing the dispersibility and enhancing the ultraviolet protection effect and the anti-adherence effect on air hazardous substances of the component (A1) and the component (A2) in the cosmetic.

The treatment amount described above means the amount based on 100 mass % in total of the titanium dioxide fine particle or the zinc oxide fine particle and the surface treatment agent. The average primary particle size $d_A$ described above and the content and the mass ratio in the cosmetic to be described later also means the average primary particle size $d_A$, the content, and the mass ratio including the surface treatment agent.

A content of the hydrophobized titanium dioxide fine particle is 5 mass % or more in the water-in-oil emulsified sunscreen cosmetic of the present invention. When a content of the hydrophobized titanium dioxide fine particles is 5 mass % or more, the ultraviolet protection effect is improved, and a high ultraviolet protection effect can be imparted even when a low content of an ultraviolet absorber is used or no ultraviolet absorber is used.

The content of the hydrophobized titanium dioxide fine particle is, from viewpoints of the ultraviolet protection effect and the like, preferably 6 mass % or more, more preferably 7 mass % or more, further more preferably 8 mass % or more, in the water-in-oil emulsified sunscreen cosmetic of the present invention, and is, from viewpoints of the absence of powdery feel, the absence of white residue, smoothness when applied and the like, preferably 25 mass % or less, more preferably 20 mass % or less, and further more preferably 15 mass % or less, in the water-in-oil emulsified sunscreen cosmetic of the present invention. Specific ranges thereof are preferably 6 mass % or more and 25 mass % or less, more preferably 7 mass % or more and 20 mass % or less, and further more preferably 8 mass % or more and 15 mass % or less, in the water-in-oil emulsified sunscreen cosmetic of the present invention. When a content of the hydrophobized titanium dioxide fine particle is 8 mass % or more, the ultraviolet protection effect is particularly improved.

A content of the hydrophobized zinc oxide fine particle is 10 mass % or more in the water-in-oil emulsified sunscreen cosmetic of the present invention. When a content of the hydrophobized zinc oxide fine particle is 10 mass % or more, the ultraviolet protection effect is improved, and a high ultraviolet protection effect can be imparted even when a low content of an ultraviolet absorber is used or no ultraviolet absorber is used.

The content of the hydrophobized zinc oxide fine particle is, from viewpoints of the ultraviolet protection effect and the like, preferably 12 mass % or more, more preferably 13 mass % or more, further more preferably 15 mass % or more, and particularly preferably 17 mass % or more, in the water-in-oil emulsified sunscreen cosmetic of the present invention, and is from viewpoints of the absence of powdery feel, the absence of white residue, smoothness when applied and the like, preferably 35 mass % or less, more preferably 30 mass % or less, and further more preferably 25 mass % or less, in the water-in-oil emulsified sunscreen cosmetic of the present invention. Specific ranges thereof are preferably 12 mass % or more and 35 mass % or less, more preferably 13 mass % or more and 30 mass % or less, further more preferably 15 mass % or more and 25 mass % or less, and particularly preferably 17 mass % or more and 25 mass % or less, in the water-in-oil emulsified sunscreen cosmetic of the present invention. When a content of the hydrophobized zinc oxide fine particle is 17 mass % or more, the ultraviolet protection effect is particularly improved.

The water-in-oil emulsified sunscreen cosmetic of the present invention can contain a component (A3) ultraviolet scattering agent other than the component (A1) or (A2). Examples of the ultraviolet scattering agent may include a hydrophobized cerium oxide fine particle, a hydrophobized iron oxide fine particle, and a hydrophobized chromium oxide fine particle. Examples of the hydrophobization treatment of the component (A3) include the same hydrophobization treatments described for the components (A1) and (A2). These ultraviolet scattering agents can be used alone, or two or more can also be used in combination.

A content of the component (A3) is preferably 0 mass % or more and 5 mass % or less, more preferably 0 mass % or more and 2.5 mass % or less, further more preferably 0 mass % or more and 1 mass % or less, further more preferably 0 mass % or more and 0.5 mass % or less, and particularly preferably 0 mass %, in the water-in-oil emulsified sunscreen cosmetic of the present invention.

<COMPONENT (B)>

The water-in-oil emulsified sunscreen cosmetic of the present invention contains (B) the divalent polyol. The "divalent polyol" means alcohol having two hydroxy groups in a molecule. Owing to the presence of the divalent polyol in the cosmetic of the present invention, a coating film after being dried is likely to be uniform, thereby the ultraviolet protection effect is excellent.

Examples of the divalent polyol include alkylene glycol such as ethylene glycol, propylene glycol, and 1,3-butylene glycol; dialkylene glycol such as diethylene glycol, and dipropylene glycol; and polyalkylene glycol such as polyethylene glycol, and polypropylene glycol. Of these, alkylene glycol and dialkylene glycol are preferable, dialkylene glycol is more preferable, and dipropylene glycol is particularly preferable, from viewpoints of the uniformity of a coating film after being dried, the ultraviolet protection effect, the absence of powdery feel and the like.

The number of carbons of the divalent polyol is preferably 1 or more and 12 or less, more preferably 2 or more and 10 or less, further more preferably 2 or more and 8 or less, and particularly preferably 4 or more and 8 or less.

For the divalent polyol, a commercial product thereof can be used, or those obtained by synthesis in accordance with a usual method can also be used. Commercial products of 1,3-butylene glycol include 1,3-butylene glycol-P (manufactured by KH Neochem Co., Ltd.). Commercial products of dipropylene glycol include DPG-RF (manufactured by ADEKA CORPORATION).

The divalent polyol can be used alone, or two or more can also be used in combination.

A content of the divalent polyol is, from viewpoints of the uniformity of a coating film after being dried, the ultraviolet protection effect, the absence of powdery feel and the like, preferably 1 mass % or more, more preferably 3 mass % or more, further more preferably 4 mass % or more, and particularly preferably 4.5 mass % or more, in the water-in-oil emulsified sunscreen cosmetic of the present invention, and is, from viewpoints of the absence of stickiness, the emulsion stability and the like, preferably 14 mass % or less, more preferably 12 mass % or less, further more preferably 10 mass % or less, and particularly preferably 8 mass % or less, in the water-in-oil emulsified sunscreen cosmetic of the present invention. Specific ranges thereof are preferably 1 mass % or more and 14 mass % or less, more preferably 3 mass % or more and 12 mass % or less, further more preferably 4 mass % or more and 10 mass % or less, and particularly preferably 4.5 mass % or more and 8 mass % or less, in the water-in-oil emulsified sunscreen cosmetic of the present invention. When a content of the divalent polyol is 1 mass % or more, the uniformity of a coating film after being dried, the ultraviolet protection effect, and the absence of powdery feel are particularly improved.

A mass ratio of the component (B) to the total of the components (A1) and (A2), [(B)/((A1)+(A2))], is, from viewpoints of the uniformity of a coating film after being dried, the ultraviolet protection effect, reducing powdery feel after the cosmetic of the present invention is applied, enhancing a smooth feel and the like, preferably 0.05 or more, more preferably 0.1 or more, and further more preferably 0.125 or more, and is, from viewpoints of the absence of stickiness and the like, preferably 0.75 or less, more preferably 0.5 or less, and further more preferably 0.4 or less. Specific ranges thereof are preferably 0.05 or more and 0.75 or less, more preferably 0.1 or more and 0.5 or less, and further more preferably 0.125 or more and 0.4 or less.

<COMPONENT (C)>

The water-in-oil emulsified sunscreen cosmetic of the present invention contains (C) the non-volatile hydrocarbon oil.

The non-volatile hydrocarbon oil can be any liquid hydrocarbon oil as long as it does not show volatility under 1 atm at 25° C. The flash point of the hydrocarbon oil, which is non-volatile under 1 atm at 25° C., is preferably 100° C. or more. Of the hydrocarbon oils which are non-volatile under 1 atm at 25° C., preferable are those having a viscosity of 300 mPa·s or less at 25° C., more preferably 150 mPa·s or less, further more preferably 100 mPa·s or less, from viewpoints of the absence of powdery feel, the absence of stickiness, and the easiness to spread. Examples of the component (C) include liquid paraffin, liquid isoparaffin, squalane and the like, and these can be used alone, or two or more thereof can also be used in combination.

The viscosity of the component (C) may be measured by using a B-type viscometer TVB-10 (manufactured by Toki Sangyo Co., Ltd.), under conditions of rotor 2, 25° C., and 30 rpm.

Commercial products of the liquid isoparaffin include Pearl Ream EX, and Pearl Ream 6 (all manufactured by NOF CORPORATION). Commercial products of squalane include NIKKOL SQUALANE (manufactured by Nippon Surfactant Industries Co., Ltd.).

A content of the non-volatile hydrocarbon oil is 2 mass % or more and 14 mass % or less in the water-in-oil emulsified sunscreen cosmetic of the present invention. When a content of the non-volatile hydrocarbon oil is in this range, the powdery feel is improved, and a smooth feel with little rough feel can be imparted.

The content of the non-volatile hydrocarbon oil is, from viewpoints of reducing powdery feel when the cosmetic of the present invention is applied, and enhancing a smooth feel when it is applied, preferably 4 mass % or more, more preferably 5 mass % or more, and further more preferably 6 mass % or more, in the water-in-oil emulsified sunscreen cosmetic of the present invention, and is, from viewpoints of the absence of an oily feel and the like, preferably 14 mass % or less, more preferably 13 mass % or less, and further more preferably 12 mass % or less, in the water-in-oil emulsified sunscreen cosmetic of the present invention. Specific ranges thereof are preferably 4 mass % or more and 14 mass % or less, more preferably 4 mass % or more and 13 mass % or less, further more preferably 5 mass % or more and 13 mass % or less, and particularly preferably 6 mass % or more and 12 mass % or less, in the water-in-oil emulsified sunscreen cosmetic of the present invention. When a content of the non-volatile hydrocarbon oil is 6 mass % or more, the absence of powdery feel is particularly improved.

A mass ratio of the component (C) to a total of the components (A1) and (A2), [(C)/((A1)+(A2))], is, from viewpoints of reducing powdery feel when the cosmetic of the present invention is applied, suppressing a rough feel, enhancing a smooth feel when it is applied, a moisturized feel when it is applied and the like, preferably 0.05 or more, more preferably 0.1 or more, further more preferably 0.2 or more, and particularly preferably 0.3 or more, and is, from viewpoints of the ultraviolet protection effect, the anti-adherence effect on air hazardous substances and the like, preferably 1.5 or less, more preferably 1 or less, further more preferably 0.75 or less, and particularly preferably 0.39 or less. Specific ranges thereof are preferably 0.05 or more and 1.5 or less, more preferably 0.1 or more and 1 or less, further more preferably 0.2 or more and 0.75 or less, and particularly preferably 0.3 or more and 0.39 or less.

<COMPONENT (D)>

The non-volatile silicone oil can be any liquid silicone oil as long as it does not show volatility under 1 atm at 25° C.

Examples of the non-volatile silicone oil include non-volatile chain polysiloxane such as dimethylpolysiloxane, methyl phenyl polysiloxane, and methyl hydrogen polysiloxane; and non-volatile cyclic polysiloxane such as tetramethyltetrahydrogenpolysiloxane. These can be used alone, or two or more can also be used in combination. Of these, dimethylpolysiloxane, and methyl phenyl polysiloxane are preferable.

The kinetic viscosity of the non-volatile silicone oil at 25° C. is, from viewpoints of a moisturized feel and the long-lasting property of skin smoothness, the absence of stickiness, and the easiness to spread, preferably 300 $mm^2/s$ or less, more preferably 150 $mm^2/s$ or less, further more preferably 100 $mm^2/s$ or less, and particularly preferably 50 $mm^2/s$ or less, and is preferably 3 $mm^2/s$ or more.

Commercial products of dimethylpolysiloxane include KF-96L-6CS, and KF-96A-10CS (all manufactured by Shin-Etsu Chemical Co., Ltd.). Commercial product of methyl phenyl polysiloxane include SH 556 Fluid (manufactured by Dow Corning Toray Co., Ltd.)

The water-in-oil emulsified sunscreen cosmetic of the present invention can optionally contain a non-volatile silicone oil, and a content of the non-volatile silicone oil is 0 mass % or more and 5 mass % or less in the water-in-oil emulsified sunscreen cosmetic of the present invention. When the content of the non-volatile silicone oil is 0 mass % or more and 5 mass % or less, the anti-adherence effect on air hazardous substances is improved.

The content of the non-volatile silicone oil is, from viewpoints of the anti-stickiness effect, the long-lasting property of skin smoothness and the like, preferably 0.1 mass % or more, and more preferably 0.5 mass % or more, in the water-in-oil emulsified sunscreen cosmetic of the present invention, and is, from viewpoints of the anti-adherence effect on air hazardous substances, the absence of an oily feel and the like, preferably 4 mass % or less, and more preferably 3 mass % or less, in the water-in-oil emulsified sunscreen cosmetic of the present invention. Specific ranges thereof are preferably 0 mass % or more and 4 mass % or less, more preferably 0 mass % or more and 3 mass % or less, further more preferably 0.1 mass % or more and 3 mass % or less, and particularly preferably 0.5 mass % or more and 3 mass % or less, in the water-in-oil emulsified sunscreen cosmetic of the present invention. When a content of the non-volatile silicone oil is 4 mass % or less or 3 mass % or less, the anti-adherence effect on air hazardous substances is particularly improved.

A mass ratio of the component (D) to the total of the components (A1) and (A2), [(D)/((A1)+(A2))], is, from viewpoints of the anti-stickiness effect, the long-lasting property of skin smoothness and the like, preferably 0 or more, more preferably 0.005 or more, further more preferably 0.01 or more, and particularly preferably 0.025 or more, and is, from viewpoints of the ultraviolet protection effect, the anti-adherence effect on air hazardous substances, the absence of an oily feel and the like, preferably 0.5 or less, more preferably 0.25 or less, further more preferably 0.2 or less, further more preferably 0.15 or less, further more preferably 0.1 or less, and particularly preferably 0.06 or less. Specific ranges thereof are preferably 0 or more and 0.5 or less, more preferably 0.005 or more and 0.25 or less, further more preferably 0.01 or more and 0.15 or less, and particularly preferably 0.025 or more and 0.1 or less.

A mass ratio of the component (D) to the component (C), [(D)/(C)], is, from viewpoints of controlling a rough feel on the skin, reducing powdery feel, and enhancing the long-lasting property of skin smoothness, preferably 0 or more, more preferably 0.05 or more, further more preferably 0.075 or more, and particularly preferably 0.1 or more, and is, from viewpoints of reducing powdery feel, enhancing a smooth feel, and improving the anti-adherence effect on air hazardous substances, preferably 1 or less, more preferably 0.75 or less, further more preferably 0.5 or less, and particularly preferably 0.2 or less. Specific ranges thereof are preferably 0 or more and 1 or less, more preferably 0.05 or more and 0.75 or less, further more preferably 0.075 or more and 0.5 or less, and particularly preferably 0.1 or more and 0.2 or less.

<COMPONENT (E)>

A content of (E) water is, from viewpoints of the emulsion stability, the absence of an oily feel and the like, preferably 1 mass % or more, more preferably 3 mass % or more, and further more preferably 5 mass % or more, in the water-in-oil emulsified sunscreen cosmetic of the present invention, and is, from viewpoints of the water resistance, the easiness to spread, the absence of a sticky feel and the like, preferably 25 mass % or less, more preferably 20 mass % or less, further more preferably 17.5 mass % or less, and particularly preferably 15 mass % or less, in the water-in-oil emulsified sunscreen cosmetic of the present invention. Specific ranges thereof are preferably 1 mass % or more and 25 mass % or less, more preferably 1 mass % or more and 20 mass % or less, further more preferably 3 mass % or more and 17.5 mass % or less, and particularly preferably 5 mass % or more and 15 mass % or less, in the water-in-oil emulsified sunscreen cosmetic of the present invention.

The water-in-oil emulsified sunscreen cosmetic of the present invention preferably further contains, other than the above components, from viewpoints of the anti-adherence effect on air hazardous substances, the emulsion stability, the dispersion stability and the like, one or more selected from the group consisting of (F) a non-volatile oil other than the components (C) or (D), (G) a volatile oil, (H) a surfactant, (I) a powder other than the components (A1) to (A3), and (J) an oil thickener, more preferably contains the components (A1), (A2), (B), (C), (E), and (F), and a content of the component (D) being 0 mass % or more and 5 mass % or less, contains the components (A1), (A2), (B), (C), (E), and (G), and a content of the component (D) being 0 mass % or more and 5 mass % or less, or contains the components (A1), (A2), (B), (C), (E), and (J), and a content of the component (D) being 0 mass % or more and 5 mass % or less, further more preferably contains the components (A1), (A2), (B), (C), and (E) to (G), and a content of the component (D) being 0 mass % or more and 5 mass % or less, and particularly preferably contains the components (A1), (A2), (B), (C), and (E) to (J), and a content of the component (D) being 0 mass % or more and 5 mass % or less.

<COMPONENT (F)>

The non-volatile oil other than the components (C) or (D) means, among liquid oils which do not show volatility under 1 atm at 25° C., those from which the components (C) or (D) and an oil-soluble ultraviolet absorber which is liquid under 1 atm at 25° C. are excluded.

The non-volatile oil other than the components (C) or (D) is preferably a non-volatile ester oil. Examples thereof include a non-volatile fatty acid ester oil such as 2-cetyl ethylhexanoate, isononyl isononanoate, isotridecyl isononanoate, isopropyl myristate, isopropyl palmitate, 2-ethylhexyl palmitate, 2-ethylhexyl stearate, and stearyl stearate; and alkyl benzoate (C12-15). Also usable as the non-volatile fatty acid ester oil are fatty acid triglycerides such as caprylic/capric triglyceride, and glyceryl tri(2-ethylhexanoate); esters of a fatty acid and neopentyl glycol such as neopentyl glycol dicaprate, and neopentyl glycol diethylhexanoate; and other polyhydric alcohol fatty acid ester oils.

Of these, from viewpoints of the anti-adherence effect on air hazardous substances, and good compatibility to the skin and the like, non-volatile fatty acid ester oils are preferable, non-volatile polyhydric alcohol fatty acid ester oils are more preferable, fatty acid triglycerides, and esters of a fatty acid and neopentyl glycol are particularly preferable.

Commercial products of isopropyl palmitate include EXCEPARL IPP (manufactured by Kao Corporation).

Commercial products of alkyl benzoate (C12-15) include FINSOLV TN (manufactured by Innospec Active Chemicals). Commercial products of glyceryl tri(2-ethylhexanoate) include EXCEPARL TGO (manufactured by Kao Corporation). Commercial products of neopentyl glycol dicaprate include ESTEMOL N-01 (manufactured by The Nisshin OilliO Group, Ltd.) Commercial products of neopentyl glycol diethylhexanoate include COSMOL 525 (manufactured by The Nisshin OilliO Group, Ltd.)

The non-volatile oil other than the components (C) or (D) can be used alone, or two or more can also be used in combination.

When a non-volatile ester oil is used as the non-volatile oil other than the components (C) or (D), a content of the non-volatile ester oil is preferably 0.5 mass % or more and 15 mass % or less, more preferably 1 mass % or more and 10 mass % or less, and particularly preferably 3 mass % or more and 7.5 mass % or less, in the water-in-oil emulsified sunscreen cosmetic of the present invention. When a content of the non-volatile ester oil is within such a range, the anti-adherence effect on air hazardous substances is further more excellent.

<COMPONENT (G)>

The volatile oil needs to be a liquid oil, which shows volatility at under 1 atm at 25° C. Examples of the volatile oil include a volatile silicone oil, and a volatile hydrocarbon oil. The flash point of the volatile hydrocarbon oil is preferably 100° C. or less, and more preferably 35° C. or more and 100° C. or less.

Examples of the volatile silicone oil include a volatile cyclic silicone oil such as octamethylcyclotetrasiloxane, and decamethylcyclopentasiloxane; a straight-chain or branched-chain volatile silicone oil such as octamethyltrisiloxane, methyl trimethicone, ethyl trisiloxane, decamethyltetrasiloxane, and volatile dimethylpolysiloxane. The kinetic viscosity of the volatile dimethylpolysiloxane at 25° C. is preferably 0.5 $mm^2/s$ or more and 2 $mm^2/s$ or less, and more preferably 0.65 $mm^2/s$ or more and 2 $mm^2/s$ or less.

Examples of the volatile hydrocarbon oil include a paraffin volatile hydrocarbon oil such as n-decane, n-undecane, and n-dodecane; an isoparaffin volatile hydrocarbon oil such as isodecane, isododecane, and a light liquid isoparaffin.

Commercial products of decamethylcyclopentasiloxane include TSF405A (manufactured by Momentive Performance Materials Japan LLC), SH245, DC345 (manufactured by Dow Corning Toray Co., Ltd.), and KF-995 (manufactured by Shin-Etsu Chemical Co., Ltd.) Commercial products of methyl trimethicone include silicone TMF-1.5 (manufactured by Shin-Etsu Chemical Co., Ltd.) Commercial products of ethyl trisiloxane include SILSOFTETS (manufactured by Momentive Performance Materials Japan LLC). Commercial products of decamethyltetrasiloxane include KF-96L-1.5CS (manufactured by Shin-Etsu Chemical Co., Ltd.) Commercial products of volatile dimethylpolysiloxane include KF-96L-2CS (manufactured by Shin-Etsu Chemical Co., Ltd.).

Commercial products of the light liquid isoparaffin include Pearl Ream 4 (manufactured by NOF CORPORATION).

The volatile oil can be used alone, or two or more can also be used in combination.

A content of the volatile oil is, from viewpoints of the easiness to spread, the absence of an oily feel and the like, preferably 0 mass % or more and 50 mass % or less, more preferably 5 mass % or more and 40 mass % or less, and particularly preferably 10 mass % or more and 35 mass % or less, in the water-in-oil emulsified sunscreen cosmetic of the present invention.

<COMPONENT (H)>

The surfactant usable can be a known surfactant such as an anionic surfactant, a cationic surfactant, a nonionic surfactant, and an amphoteric surfactant but is preferably, from viewpoints of the water resistance and the easiness to mix, a nonionic surfactant, and more preferably a nonionic surfactant having an HLB of 8 or less (preferably HLB of from 1 to 7, more preferably HLB of from 2 to 6, and particularly preferably HLB of from 3 to 5). The surfactant is preferably a surfactant, which is liquid at 25° C.

HLB herein is the indicator showing the hydrophilic-lipophilic balance, and is defined by the following equation of Oda and Teramura et al.

$$HLB=(\Sigma \text{ inorganic value}/\Sigma \text{organic value})\times 10$$

Examples of the nonionic surfactant include a polyhydric alcohol fatty acid ester surfactant, a polyoxyethylene fatty acid ester surfactant, a polyether-modified silicone surfactant, and a polyoxyethylene alkyl ether surfactant. Of these, a polyhydric alcohol fatty acid ester surfactant, and a polyether-modified silicone surfactant are preferable.

Examples of the polyhydric alcohol fatty acid ester surfactant include a glycerin fatty acid ester surfactant, a sorbitan fatty acid ester surfactant, a diglycerin fatty acid ester surfactant, a polyglycerin fatty acid ester surfactant, and a propylene glycol fatty acid ester surfactant. Of these, a sorbitan fatty acid ester surfactant is preferable, and a sorbitan monofatty acid ester surfactant is particularly preferable. Specifically, examples thereof include sorbitan monostearate, sorbitan monoisostearate, and sorbitan monooleate.

The polyether-modified silicone surfactant is preferably a polyoxyethylenemethylpolysiloxane copolymer, and a poly(oxyethyleneoxypropylene) methylpolysiloxane copolymer. Specifically, examples thereof include PEG-3 dimethicone, PEG-9 dimethicone, and PEG-10 dimethicone.

The surfactant can be used alone, or two or more can also be used in combination.

A content of the surfactant is, from viewpoints of the dispersibility of powders, the enhancement of emulsion stability, the absence of a sticky feel and the like, preferably 0.2 mass % or more and 10 mass % or less, more preferably 0.5 mass % or more and 8 mass % or less, and particularly preferably 1 mass % or more and 5 mass % or less, in the water-in-oil emulsified sunscreen cosmetic of the present invention.

<COMPONENT (I)>

Examples of the powder other than the components (A1) to (A3) include hydrophobized talc, a cellulose particle, porous silica, a crosslinked (meth)acrylic acid ester resin particle, and a silicone resin particle. These can be used alone, or two or more can also be used in combination.

A content of the powder other than the components (A1) to (A3) is, from viewpoints of the absence of powdery feel, the long-lasting property of skin smoothness, the absence of a sticky feel and the like, preferably 0.2 mass % or more and 10 mass % or less, more preferably 0.5 mass % or more and 8 mass % or less, and particularly preferably 1 mass % or more and 5 mass % or less, in the water-in-oil emulsified sunscreen cosmetic of the present invention.

<COMPONENT (J)>

Examples of the oil thickener include polyglyceryl isostearate, glyceryl (behenate/eicosadioate), and organic modified clay minerals, in addition to sugar fatty acid ester oil thickeners such as inulin fatty acid ester, and dextrin fatty acid ester. These can be used alone, or two or more can also be used in combination.

Of these, a sugar fatty acid ester oil thickener is preferable from viewpoints of the absence of an oily feel, the long-lasting property of skin smoothness and the like. The fatty acid residue of the sugar fatty acid ester oil thickener is preferably a straight-chain or branched-chain saturated fatty acid residue. The number of carbons of the fatty acid residue is preferably 8 to 24, more preferably 12 to 22, and particularly preferably 14 to 20.

The sugar fatty acid ester oil thickener is preferably dextrin fatty acid ester. Specifically, examples thereof include dextrin myristate, dextrin palmitate, dextrin stearate, dextrin (palmitate/2-ethylhexanoate), and dextrin (palmitate/hexyldecanoate).

A content of the oil thickener is, from viewpoints of the absence of an oily feel, the absence of a sticky feel, the long-lasting property of skin smoothness and the like, preferably 0.05 mass % or more and 5 mass % or less, more preferably 0.1 mass % or more and 4 mass % or less, and particularly preferably 0.2 mass % or more and 3 mass % or less, in the water-in-oil emulsified sunscreen cosmetic of the present invention.

The water-in-oil emulsified sunscreen cosmetic of the present invention can optionally contain, other than the above components, a coat-forming agent such as trimethylsiloxysilicate; a polyol other than the component (B); lower alcohol; waxes; a preservative; a perfume; a pH regulator; a moisturizer; a feel enhancer; a sebum absorbent; a viscosity modifier; vitamins such as tocopherol; terpenes such as carotene. These can be used alone, or two or more can also be used in combination.

A content of the coat-forming agent is preferably 0 mass % or more and 0.075 mass % or less, more preferably 0 mass % or more and 0.01 mass % or less, and particularly preferably 0 mass %, in the water-in-oil emulsified sunscreen cosmetic of the present invention.

Examples of the dosage form of the water-in-oil emulsified sunscreen cosmetic of the present invention include a non-solid form such as an emulsion, a cream, a paste, and a gel.

The water-in-oil emulsified sunscreen cosmetic of the present invention can be applied to a skin (preferably a skin excluding scalp, more preferably a face, a body, a limb and the like) and used as a sunscreen agent. The method for using the cosmetic is not particularly limited, and applying the cosmetic by hand or with an applicator is preferred.

The water-in-oil emulsified sunscreen cosmetic of the present invention can be produced in accordance with a usual method.

The water-in-oil emulsified sunscreen cosmetic of the present invention hardly allows air hazardous substances to adhere to a coating film thereof, and has an excellent ultraviolet protection effect, while having a non-powdery pleasant use impression. The present inventor presumes that the grounds for exhibiting such an excellent ultraviolet protection effect may be attributed to a coating film which is likely to be uniform after being dried, thereby imparting the ultraviolet protection effect evenly.

The water-in-oil emulsified sunscreen cosmetic of the present invention can exhibit a high ultraviolet protection effect even when a low content of an ultraviolet absorber is used or no ultraviolet absorber is used. A content of the ultraviolet absorber is preferably 0 mass % or more and 5 mass % or less, more preferably 0 mass % or more and 2.5 mass % or less, further more preferably 0 mass % or more and 1 mass % or less, further more preferably 0 mass % or more and 0.5 mass % or less, and particularly preferably 0 mass %, in the water-in-oil emulsified sunscreen cosmetic of the present invention.

The present invention further discloses the following cosmetics and the like with respect to the above-mentioned embodiments.

<1> A water-in-oil emulsified sunscreen cosmetic, comprising the following components (A1), (A2), (B), and (C), with a content of (D) a non-volatile silicone oil being 0 mass % or more and 5 mass % or less:

(A1) 5 mass % or more of a hydrophobized titanium dioxide fine particle, (A2) 10 mass % or more of a hydrophobized zinc oxide fine particle, (B) a divalent polyol, and (C) 2 mass % or more and 14 mass % or less of a non-volatile hydrocarbon oil.

<2> The water-in-oil emulsified sunscreen cosmetic according to <1>, wherein an average primary particle size $d_A$ of the components (A1) and (A2) is preferably 1 nm or more, more preferably 5 nm or more, and preferably 100 nm or less, and more preferably 80 nm or less.

<3> The water-in-oil emulsified sunscreen cosmetic according to <1>, wherein an average primary particle size $d_A$ of the components (A1) and (A2) is preferably 1 nm or more, and more preferably 7 nm or more, and preferably 200 nm or less, more preferably 80 nm or less, and further more preferably 50 nm or less.

<4> The water-in-oil emulsified sunscreen cosmetic according to <1>, wherein an average primary particle size $d_A$ of the components (A1) and (A2) is preferably 1 nm or more and 200 nm or less, more preferably 5 nm or more and 200 nm or less, further more preferably 5 nm or more and 100 nm or less, further more preferably 7 nm or more and 100 nm or less, further more preferably 7 nm or more and 80 nm or less, and particularly preferably 7 nm or more and 50 nm or less.

<5> The water-in-oil emulsified sunscreen cosmetic according to any of <1> to <4>, wherein hydrophobization of the component (A1) is preferably a hydrophobization treatment selected from the group consisting of silicone treatment, alkylalkoxysilane treatment, fatty acid treatment, treatment with a fluorine-containing compound, amino acid treatment, and alkyl phosphate ester treatment, and more preferably fatty acid treatment.

<6> The water-in-oil emulsified sunscreen cosmetic according to any of <1> to <5>, wherein hydrophobization of the component (A2) is preferably a hydrophobization treatment selected from the group consisting of silicone treatment, alkylalkoxysilane treatment, fatty acid treatment, treatment with a fluorine-containing compound, amino acid treatment, and alkyl phosphate ester treatment, and more preferably a hydrophobization treatment selected from the group consisting of silicone treatment and alkylalkoxysilane treatment.

<7> The water-in-oil emulsified sunscreen cosmetic according to any of <1> to <6>, wherein a content of the component (A1) is preferably 6 mass % or more, more preferably 7 mass % or more, and further more preferably 8 mass % or more, in the water-in-oil emulsified sunscreen cosmetic, and preferably 25 mass % or less, more preferably 20 mass % or less, and further more preferably 15 mass % or less, in the water-in-oil emulsified sunscreen cosmetic.

<8> The water-in-oil emulsified sunscreen cosmetic according to any of <1> to <6>, wherein a content of the component (A1) is preferably 6 mass % or more and 25 mass % or less, more preferably 7 mass % or more and 20 mass % or less, and further more preferably 8 mass % or more and 15 mass % or less, in the water-in-oil emulsified sunscreen cosmetic.

<9> The water-in-oil emulsified sunscreen cosmetic according to any of <1> to <8>, wherein a content of the component (A2) is preferably 12 mass % or more, more preferably 13 mass % or more, further more preferably 15 mass % or more, and particularly preferably 17 mass % or more, in the water-in-oil emulsified sunscreen cosmetic, and preferably 35 mass % or less, more preferably 30 mass % or less, and further more preferably 25 mass % or less, in the water-in-oil emulsified sunscreen cosmetic.

<10> The water-in-oil emulsified sunscreen cosmetic according to any of <1> to <8>, wherein a content of the component (A2) is preferably 12 mass % or more and 35 mass % or less, more preferably 13 mass % or more and 30 mass % or less, further more preferably 15 mass % or more and 25 mass % or less, and particularly preferably 17 mass % or more and 25 mass % or less, in the water-in-oil emulsified sunscreen cosmetic.

<11> The water-in-oil emulsified sunscreen cosmetic according to any of <1> to <10>, wherein the component (B) is preferably one or more selected from the group consisting of alkylene glycol, dialkylene glycol, and polyalkylene glycol, more preferably one or more selected from the group consisting of alkylene glycol, and dialkylene glycol, further more preferably dialkylene glycol, and particularly preferably dipropylene glycol.

<12> The water-in-oil emulsified sunscreen cosmetic according to any of <1> to <11>, wherein the number of carbons of the component (B) is preferably 1 or more and 12 or less, more preferably 2 or more and 10 or less, further more preferably 2 or more and 8 or less, and particularly preferably 4 or more and 8 or less.

<13> The water-in-oil emulsified sunscreen cosmetic according to any of <1> to <12>, wherein a content of the component (B) preferably 1 mass % or more, more preferably 3 mass % or more, further more preferably 4 mass % or more, and particularly preferably 4.5 mass % or more, in the water-in-oil emulsified sunscreen cosmetic, and preferably 14 mass % or less, more preferably 12 mass % or less, further more preferably 10 mass % or less, and particularly preferably 8 mass % or less, in the water-in-oil emulsified sunscreen cosmetic.

<14> The water-in-oil emulsified sunscreen cosmetic according to any of <1> to <12>, wherein a content of the component (B) is preferably 1 mass % or more and 14 mass % or less, more preferably 3 mass % or more and 12 mass % or less, further more preferably 4 mass % or more and 10 mass % or less, and particularly preferably 4.5 mass % or more and 8 mass % or less, in the water-in-oil emulsified sunscreen cosmetic.

<15> The water-in-oil emulsified sunscreen cosmetic according to any of <1> to <14>, wherein a mass ratio of the component (B) to a total of the components (A1) and (A2), [(B)/((A1)+(A2))], is preferably 0.05 or more, more preferably 0.1 or more, and further more preferably 0.125 or more, and preferably 0.75 or less, more preferably 0.5 or less, and further more preferably 0.4 or less.

<16> The water-in-oil emulsified sunscreen cosmetic according to any of <1> to <14>, wherein a mass ratio of the component (B) to a total of the components (A1) and (A2), [(B)/((A1)+(A2))], is preferably 0.05 or more and 0.75 or less, more preferably 0.1 or more and 0.5 or less, and further more preferably 0.125 or more and 0.4 or less.

<17> The water-in-oil emulsified sunscreen cosmetic according to any of <1> to <16>, wherein a flash point of the component (C) is preferably 100° C. or more.

<18> The water-in-oil emulsified sunscreen cosmetic according to any of <1> to <17>, wherein a viscosity of the component (C) at 25° C. is preferably 300 mPa·s or less, more preferably 150 mPa·s or less, and further more preferably 100 mPa·s or less.

<19> The water-in-oil emulsified sunscreen cosmetic according to any of <1> to <18>, wherein the component (C) is preferably one or more selected from the group consisting of liquid paraffin, liquid isoparaffin, and squalane.

<20> The water-in-oil emulsified sunscreen cosmetic according to any of <1> to <19>, wherein a content of the component (C) is preferably 4 mass % or more, more preferably 5 mass % or more, and further more preferably 6 mass % or more, in the water-in-oil emulsified sunscreen cosmetic, and preferably 14 mass % or less, more preferably 13 mass % or less, and further more preferably 12 mass % or less, in the water-in-oil emulsified sunscreen cosmetic.

<21> The water-in-oil emulsified sunscreen cosmetic according to any of <1> to <19>, wherein a content of the component (C) is preferably 4 mass % or more and 14 mass % or less, more preferably 4 mass % or more and 13 mass % or less, further more preferably 5 mass % or more and 13 mass % or less, and particularly preferably 6 mass % or more and 12 mass % or less, in the water-in-oil emulsified sunscreen cosmetic.

<22> The water-in-oil emulsified sunscreen cosmetic according to any of <1> to <21>, wherein a mass ratio of the component (C) to a total of the components (A1) and (A2), [(C)/((A1)+(A2))], is preferably 0.05 or more, more preferably 0.1 or more, further more preferably 0.2 or more, and particularly preferably 0.3 or more, and preferably 1.5 or less, more preferably 1 or less, further more preferably 0.75 or less, and particularly preferably 0.39 or less.

<23> The water-in-oil emulsified sunscreen cosmetic according to any of <1> to <21>, wherein a mass ratio of the component (C) to a total of the components (A1) and (A2), [(C)/((A1)+(A2))], is preferably 0.05 or more and 1.5 or less, more preferably 0.1 or more and 1 or less, further more preferably 0.2 or more and 0.75 or less, and particularly preferably 0.3 or more and 0.39 or less.

<24> The water-in-oil emulsified sunscreen cosmetic according to any of <1> to <23>, wherein the component (D) is preferably one or more non-volatile silicone oils selected from the group consisting of non-volatile chain polysiloxane and non-volatile cyclic polysiloxane, more preferably one or more non-volatile silicone oils selected from the group consisting of dimethylpolysiloxane, methyl phenyl polysiloxane, methyl hydrogen polysiloxane, and tetramethyltetrahydrogenpolysiloxane, and particularly preferably one or more non-volatile silicone oils selected from the group consisting of dimethylpolysiloxane, and methyl phenyl polysiloxane.

<25> The water-in-oil emulsified sunscreen cosmetic according to any of <1> to <24>, wherein a kinetic viscosity of the component (D) at 25° C. is preferably 300 $mm^2/s$ or less, more preferably 150 $mm^2/s$ or less, further more preferably 100 $mm^2/s$ or less, and particularly preferably 50 $mm^2/s$ or less, and preferably 3 $mm^2/s$ or more.

<26> The water-in-oil emulsified sunscreen cosmetic according to any of <1> to <25>, wherein a content of the component (D) is preferably 0.1 mass % or more, and more preferably 0.5 mass % or more, in the water-in-oil emulsified sunscreen cosmetic, and preferably 4 mass % or less, and more preferably 3 mass % or less, in the water-in-oil emulsified sunscreen cosmetic.

<27> The water-in-oil emulsified sunscreen cosmetic according to any of <1> to <25>, wherein a content of the component (D) is preferably 0 mass % or more and 4 mass % or less, more preferably 0 mass % or more and 3 mass % or less, further more preferably 0.1 mass % or more and 3 mass % or less, and particularly preferably 0.5 mass % or more and 3 mass % or less, in the water-in-oil emulsified sunscreen cosmetic.

<28> The water-in-oil emulsified sunscreen cosmetic according to any of <1> to <27>, wherein a mass ratio of the component (D) to a total of the components (A1) and (A2), [(D)/((A1)+(A2))], is preferably 0 or more, more preferably 0.005 or more, further more preferably 0.01 or more, and particularly preferably 0.025 or more, and preferably 0.5 or less, more preferably 0.25 or less, further more preferably 0.2 or less, further more preferably 0.15 or less, further more preferably 0.1 or less, and particularly preferably 0.06 or less.

<29> The water-in-oil emulsified sunscreen cosmetic according to any of <1> to <27>, wherein a mass ratio of the component (D) to a total of the components (A1) and (A2), [(D)/((A1)+(A2))], is preferably 0 or more and 0.5 or less, more preferably 0.005 or more and 0.25 or less, further more preferably 0.01 or more and 0.15 or less, and particularly preferably 0.025 or more and 0.1 or less.

<30> The water-in-oil emulsified sunscreen cosmetic according to any of <1> to <29>, wherein a mass ratio of the component (D) to the component (C), [(D)/(C)], is preferably 0 or more, more preferably 0.05 or more, further more preferably 0.075 or more, and particularly preferably 0.1 or more, and preferably 1 or less, more preferably 0.75 or less, further more preferably 0.5 or less, and particularly preferably 0.2 or less.

<31> The water-in-oil emulsified sunscreen cosmetic according to any of <1> to <29>, wherein a mass ratio of the component (D) to the component (C), [(D)/(C)], is preferably 0 or more and 1 or less, more preferably 0.05 or more and 0.75 or less, further more preferably 0.075 or more and 0.5 or less, and particularly preferably 0.1 or more and 0.2 or less.

<32> The water-in-oil emulsified sunscreen cosmetic according to any of <1> to <31>, wherein a content of (E) water is preferably 1 mass % or more, more preferably 3 mass % or more, and further more preferably 5 mass % or more, in the water-in-oil emulsified sunscreen cosmetic, and preferably 25 mass % or less, more preferably 20 mass % or less, further more preferably 17.5 mass % or less, and particularly preferably 15 mass % or less, in the water-in-oil emulsified sunscreen cosmetic.

<33> The water-in-oil emulsified sunscreen cosmetic according to any of <1> to <31>, wherein a content of (E) water is preferably 1 mass % or more and 25 mass % or less, more preferably 1 mass % or more and 20 mass % or less, further more preferably 3 mass % or more and 17.5 mass % or less, and particularly preferably 5 mass % or more and 15 mass % or less, in the water-in-oil emulsified sunscreen cosmetic.

<34> The water-in-oil emulsified sunscreen cosmetic according to any of <1> to <33>, preferably further containing one or more selected from the group consisting of (F) a non-volatile oil other than the components (C) or (D), (G) a volatile oil, (H) a surfactant, (I)

a powder other than the components (A1) to (A3), and (J) an oil thickener, more preferably containing the components (A1), (A2), (B), (C), (E), and (F), and a content of the component (D) being 0 mass % or more and 5 mass % or less, containing the components (A1), (A2), (B), (C), (E), and (G), and a content of the component (D) being 0 mass % or more and 5 mass % or less, or containing the components (A1), (A2), (B), (C), (E), and (J), and a content of the component (D) being 0 mass % or more and 5 mass % or less, further more preferably containing the components (A1), (A2), (B), (C), and (E) to (G), and a content of the component (D) being 0 mass % or more and 5 mass % or less, and particularly preferably containing the components (A1), (A2), (B), (C), and (E) to (J), and a content of the component (D) being 0 mass % or more and 5 mass % or less.

<35> The water-in-oil emulsified sunscreen cosmetic according to any of <1> to <34>, which is preferably in a dosage form of an emulsion, a cream, a paste, or a gel.

<36> The water-in-oil emulsified sunscreen cosmetic according to any of <1> to <35>, wherein a content of an ultraviolet absorber is preferably 0 mass % or more and 5 mass % or less, more preferably 0 mass % or more and 2.5 mass % or less, further more preferably 0 mass % or more and 1 mass % or less, further more preferably 0 mass % or more and 0.5 mass % or less, and particularly preferably 0 mass %, in the water-in-oil emulsified sunscreen cosmetic.

EXAMPLES

Hereinafter, the present invention will be described in detail in reference to examples, but the present invention is not limited to these examples. In the present examples, measurements and evaluations were carried out by the following methods.

(Measurement and Evaluation Methods)

(1) Ultraviolet Protection Effect (SPF Value)

On a PMMA plate, each cosmetic was applied uniformly to be 2 mg/cm$^2$, and the plate was dried for 15 minutes in a cool and dark space. After the drying was completed, by using an SPF analyzer (SPF 290S plus, manufactured by Optometricus USA, Inc.), transmittances (%) of absorption spectra (wavelength 350 nm) at the total of nine points of the midpoint, each of the vertexes, and the midpoints of the sides connecting each of the vertexes of the square PMMA plate were measured to determine the average value of the transmittances of the nine points. An SPF value was calculated from the average value (%) of the transmittances and evaluation was carried out by the following criteria.

(Evaluation Criteria of the Ultraviolet Protection Effect)

AA: SPF 75 or more

A: SPF 67 or more and less than 75

B: SPF 60 or more and less than 67

C: Less than SPF 60

(2) Anti-Adherence Effect on Air Hazardous Substance

Each of the cosmetics was applied to a white artificial leather (product name "Laforet S2923", manufactured by OKAMOTO INDUSTRIES, INC.) as a substitute for the skin such that an applied amount of the components (A1) and (A2) was 0.12 mg/cm$^2$, and allowed to stand at room temperature overnight to dry.

The above artificial leather surface onto which each of the cosmetics was applied was exposed into air blowing environment of air hazardous substance for evaluation to measure the color difference ΔE before and after the exposure using a colorimeter by the following method.

[Measurement of Color Difference ΔE]

$L_1$*, $a_1$*, and $b_1$* values of the artificial leather surface before the exposure were measured by using a colorimeter (product name "CM-2002", manufactured by KONICA MINOLTA, INC.).

Separately, in a glove bag (model number "3-118-01", manufactured by AS ONE Corporation), an air blower (product name "Silky Wind 9ZF002RH02", size: 129×106×83 mm, manufactured by Rhythm Watch Co., Ltd.) and a mesh screen sieve (test sieve, JIS Z 8801, frame dimension: φ100×45 H, aperture: 106 μm, manufactured by Tokyo Screen Co., Ltd.) were fixed. The installation height of the mesh screen sieve was 17 cm.

Then, the artificial leather (5 cm×4 cm) onto which the test sample cosmetic was applied was attached to a support plate such that the lower end of the artificial leather was located at a height of 11 cm. The distance between the applied surface of the artificial leather attached to the support plate and the air blower was 15 cm, and the applied surface of the artificial leather was set perpendicular to the air blowing direction of the air blower such that the height of the blade center of the air blower aligned with the height of the artificial leather at the center as shown in FIG. 1.

The glove bag had a temperature of 25° C. and a relative humidity of 57% RH inside thereof, and 50 mg of a graphite powder (product name "J-CPB", average particle size: 5.5 μm, manufactured by Nippon Graphite Industries, Co., Ltd.) as an air hazardous substance for evaluation was allowed to fall, while classified, from the mesh screen sieve for 1 minute to the front of the outlet of the air blower with wind scale set to 1 using a brush for sieve cleaning (product name "JNB-5", brush diameter 53 μm, manufactured by Tokyo Screen Co., Ltd.), thereby exposing the surface onto which each cosmetic was applied to the air blowing environment of the air hazardous substance for evaluation.

Subsequently, $L_2$*, $a_2$*, and b2* values of the artificial leather surface after the exposure were measured by using the above colorimeter to determine the color difference ΔE value by the following equation (I).

$$\Delta E=[(L_1{*}-L_2{*})^2+(a_1{*}-a_2{*})^2+(b_1{*}-b_2{*})^2]^{0.5} \quad \text{(I)}$$

The above procedure was carried out three times for each test sample, and the average value of the color difference ΔE of the artificial leather onto which the test sample cosmetic was applied was defined as ΔEt. Further, the same procedure as above was also carried out three times for an artificial leather as a standard sample onto which the cosmetic was not applied, and the average value of color differences ΔE was defined as ΔEs to calculate the anti-adherence rate by the following equation (II). As the anti-adherence rate is higher, the anti-adherence effect on the air hazardous substance is better.

$$\text{Anti-adherence rate of air hazardous substance } (\%)=100\times(\Delta Es-\Delta Et)/\Delta Es \quad \text{(II)}$$

(Evaluation Criteria on the Anti-Adherence Effect on Air Hazardous Substance)

AA: Anti-adherence rate is 50% or more

A: Anti-adherence rate is 30% or more and less than 50%

B: Anti-adherence rate is 10% or more and less than 30%

C: Anti-adherence rate is less than 10%

(3) Absence of Powdery Feel when the Cosmetic is Applied

To two panelists was applied 0.02 mL of each cosmetic to an area having a diameter of 3 cm at the inner forearm. At this time, the panelists judged the absence of powdery feel when the cosmetic is applied by the following criteria, and the average score of the two panelists was calculated. The average score of more than 3 points was evaluated as AA, the average score of more than 2 points and 3 points or less was evaluated as A, the average score of more than 1 point and 2 points or less was evaluated as B, and the average score of 1 point or less was evaluated as C.

4 Points: Powdery feel is not perceived at all

3 Points: Powdery feel is hardly perceived

2 Points: Neutral

1 Point: Powdery feel is slightly perceived

0 Points: Strong powdery feel is perceived

Examples 1 to 7 and Comparative Examples 1 to 6

The water-in-oil emulsified sunscreen cosmetics of Examples 1 to 7 and Comparative Examples 1 to 6 were produced by a usual method in accordance with the formulae shown in Table 1 to Table 2, and the above measurements and evaluations were carried out. The results are shown in Table 1 to Table 2.

TABLE 1

| | Components (mass %) | | Example 1 | Example 2 | Example 3 | Example 4 | Example 5 | Example 6 | Example 7 |
|---|---|---|---|---|---|---|---|---|---|
| (A1) | Aluminum stearate-coated titanium dioxide *1 | | 10.0 | 10.0 | 7.0 | 10.0 | 10.0 | 10.0 | 10.0 |
| (A2) | Silicone-coated zinc oxide *2 | | 19.0 | | 19.0 | 16.0 | 19.0 | 19.0 | 19.0 |
| | Octyltriethoxysilane-coated zinc oxide *3 | | | 19.0 | | | | | |
| (D) | Non-volatile dimethylpolysiloxane *4 | | 1.5 | 1.5 | 1.5 | 1.5 | 1.5 | 4.0 | 1.5 |
| (C) | Liquid isoparaffin *5 | | 7.0 | 7.0 | 7.0 | 7.0 | 7.0 | 7.0 | 5.0 |
| | Squalane *6 | | 3.5 | 3.5 | 3.5 | 3.5 | 3.5 | 3.5 | |
| (H) | Polyoxyethylene□methylpolysiloxane copolymer *7 | | 1.5 | 1.5 | 1.5 | 1.5 | 1.5 | 1.5 | 1.5 |
| | Polyoxyethylene□methylpolysiloxane copolymer *8 | | 1.4 | 1.4 | 1.4 | 1.4 | 1.4 | 1.4 | 1.4 |
| (J) | Dextrin palmitate *9 | | 0.2 | 0.2 | 0.2 | 0.2 | 0.2 | 0.2 | 0.2 |
| (I) | Silicone-coated talc *10 | | 4.0 | 4.0 | 4.0 | 4.0 | 4.0 | 4.0 | 4.0 |
| (F) | Neopentyl glycol di(2-ethylhexanoate) *11 | | 1.5 | 1.5 | 1.5 | 1.5 | 1.5 | 1.5 | 1.5 |
| | Neopentyl glycol dicaprate *12 | | 3.0 | 3.0 | 3.0 | 3.0 | 3.0 | 3.0 | 3.0 |
| (G) | Light liquid isoparaffin *13 | | 5.0 | 5.0 | 5.0 | 5.0 | 5.0 | 5.0 | 5.0 |
| | Volatile dimethylpolysiloxane *14 | | 29.8 | 29.8 | 32.8 | 32.8 | 29.8 | 27.3 | 35.3 |
| (B) | Dipropylene glycol *15 | | 5.0 | 5.0 | 5.0 | 5.0 | 3.0 | 5.0 | 5.0 |
| | Glycerin | | | | | | | | |
| (E) | Water | | 7.6 | 7.6 | 7.6 | 7.6 | 9.6 | 7.6 | 7.6 |
| | Total (mass %) | | 100.0 | 100.0 | 100.0 | 100.0 | 100.0 | 100.0 | 100.0 |
| | Component (A1) content | | 10.0 | 10.0 | 7.0 | 10.0 | 10.0 | 10.0 | 10.0 |
| | Component (A2) content | | 19.0 | 19.0 | 19.0 | 16.0 | 19.0 | 19.0 | 19.0 |
| | Component (B) content | | 5.0 | 5.0 | 5.0 | 5.0 | 3.0 | 5.0 | 5.0 |
| | Component (C) content | | 10.5 | 10.5 | 10.5 | 10.5 | 10.5 | 10.5 | 5.0 |
| | Component (D) content | | 1.5 | 1.5 | 1.5 | 1.5 | 1.5 | 4.0 | 1.5 |
| | Mass ratio [(B)/((A1) + (A2))] | | 0.17 | 0.17 | 0.19 | 0.19 | 0.10 | 0.17 | 0.17 |
| | Mass ratio [(C)/((A1) + (A2))] | | 0.36 | 0.36 | 0.40 | 0.40 | 0.36 | 0.36 | 0.17 |
| | Mass ratio [(D)/((A1) + (A2))] | | 0.05 | 0.05 | 0.06 | 0.06 | 0.05 | 0.14 | 0.05 |
| | Mass ratio [(D)/(C)] | | 0.14 | 0.14 | 0.14 | 0.14 | 0.14 | 0.38 | 0.30 |
| UV protection effect (SPF) | | Measured value | 84 | 92 | 64 | 65 | 74 | 75 | 87 |
| | | Evaluation | AA | AA | B | B | A | AA | AA |
| Anti-adherence effect on air hazardous substance | | Measured value (%) | 61 | 70 | 60 | 61 | 62 | 34 | 88 |
| | | Evaluation | AA | AA | AA | AA | AA | A | AA |
| | Absence of powdery feel | | AA | AA | AA | AA | A | AA | B |

TABLE 2

| | Components (mass %) | Comparative Example 1 | Comparative Example 2 | Comparative Example 3 | Comparative Example 4 | Comparative Example 5 | Comparative Example 6 |
|---|---|---|---|---|---|---|---|
| (A1) | Aluminum stearate-coated titanium dioxide *1 | 3.0 | 10.0 | 10.0 | 10.0 | 10.0 | 10.0 |
| (A2) | Silicone-coated zinc oxide *2 | 19.0 | 8.0 | 19.0 | 19.0 | 19.0 | 19.0 |
| | Octyltriethoxysilane-coated zinc oxide *3 | | | | | | |
| (D) | Non-volatile dimethylpolysiloxane *4 | 1.5 | 1.5 | 1.5 | 9.0 | 1.5 | 1.5 |
| (C) | Liquid isoparaffin *5 | 7.0 | 7.0 | 7.0 | 7.0 | 1.0 | 7.5 |
| | Squalane *6 | 3.5 | 3.5 | 3.5 | 3.5 | | 10.0 |
| (H) | Polyoxyethylene□methylpolysiloxane copolymer *7 | 1.5 | 1.5 | 1.5 | 1.5 | 1.5 | 1.5 |
| | Polyoxyethylene□methylpolysiloxane copolymer *8 | 1.4 | 1.4 | 1.4 | 1.4 | 1.4 | 1.4 |
| (J) | Dextrin palmitate *9 | 0.2 | 0.2 | 0.2 | 0.2 | 0.2 | 0.2 |
| (I) | Silicone-coated talc *10 | 4.0 | 4.0 | 4.0 | 4.0 | 4.0 | 4.0 |
| (F) | Neopentyl glycol di(2-ethylhexanoate) *11 | 1.5 | 1.5 | 1.5 | 1.5 | 1.5 | 1.5 |
| | Neopentyl glycol dicaprate *12 | 3.0 | 3.0 | 3.0 | 3.0 | 3.0 | 3.0 |

TABLE 2-continued

| | Components (mass %) | | Comparative Example 1 | Comparative Example 2 | Comparative Example 3 | Comparative Example 4 | Comparative Example 5 | Comparative Example 6 |
|---|---|---|---|---|---|---|---|---|
| (G) | Light liquid isoparaffin *13 | | 5.0 | 5.0 | 5.0 | 5.0 | 5.0 | 5.0 |
| | Volatile dimethylpolysiloxane *14 | | 36.8 | 40.8 | 29.8 | 22.3 | 39.3 | 22.8 |
| (B) | Dipropylene glycol *15 | | 5.0 | 5.0 | | 5.0 | 5.0 | 5.0 |
| | Glycerin | | | | 5.0 | | | |
| (E) | Water | | 7.6 | 7.6 | 7.6 | 7.6 | 7.6 | 7.6 |
| | Total (mass %) | | 100.0 | 100.0 | 100.0 | 100.0 | 100.0 | 100.0 |
| | Component (A1) content | | 3.0 | 10.0 | 10.0 | 10.0 | 10.0 | 10.0 |
| | Component (A2) content | | 19.0 | 8.0 | 19.0 | 19.0 | 19.0 | 19.0 |
| | Component (B) content | | 5.0 | 5.0 | 0.0 | 5.0 | 5.0 | 5.0 |
| | Component (C) content | | 10.5 | 10.5 | 10.5 | 10.5 | 1.0 | 17.5 |
| | Component (D) content | | 1.5 | 1.5 | 1.5 | 9.0 | 1.5 | 1.5 |
| | Mass ratio [(B)/((A1) + (A2))] | | 0.23 | 0.28 | 0.00 | 0.17 | 0.17 | 0.17 |
| | Mass ratio [(C)/((A1) + (A2))] | | 0.48 | 0.58 | 0.36 | 0.36 | 0.03 | 0.60 |
| | Mass ratio [(D)/((A1) + (A2))] | | 0.07 | 0.08 | 0.05 | 0.31 | 0.05 | 0.05 |
| | Mass ratio [(D)/(C)] | | 0.14 | 0.14 | 0.14 | 0.86 | 1.50 | 0.09 |
| UV protection effect (SPF) | | Measured value | 20 | 23 | 57 | 88 | 66 | 94 |
| | | Evaluation | C | C | C | AA | B | AA |
| Anti-adherence effect on air hazardous substance | | Measured value (%) | 48 | 29 | 48 | −26 | 91 | −94 |
| | | Evaluation | A | B | A | C | AA | C |
| | Absence of powdery feel | | AA | AA | A | AA | C | A |

The symbols in the tables mean as follows, respectively.

*1: MT-100TV (average primary particle size $d_A$: 15 nm, manufactured by TAYCA CORPORATION)

*2: MZX-304R3M (average primary particle size $d_A$: 35 nm, manufactured by TAYCA CORPORATION)

*3: MZX-3040TS (average primary particle size $d_A$: 35 nm, manufactured by TAYCA CORPORATION)

*4: KF-96L-6CS (manufactured by Shin-Etsu Chemical Co., Ltd.)

*5: Pearl Ream EX (manufactured by NOF CORPORATION)

*6: NIKKOL SQUALANE (manufactured by NIPPON SURFACTANT INDUSTRIES CO., LTD.)

*7: KF-6015 (manufactured by Shin-Etsu Chemical Co., Ltd.)

*8: KF-6017 (manufactured by Shin-Etsu Chemical Co., Ltd.)

*9: Rheopearl KL2 (manufactured by Chiba Flour Milling Co., Ltd.)

*10: SI-Talc JA-46R (manufactured by Miyoshi Kasei, Inc.)

*11: COSMOL 525 (manufactured by The Nisshin OilliO Group, Ltd.)

*12: ESTEMOL N-01 (manufactured by The Nisshin OilliO Group, Ltd.)

*13: Pearl Ream 4 (manufactured by NOF CORPORATION)

*14: KF-96L-2CS (manufactured by Shin-Etsu Chemical Co., Ltd.)

*15: DPG-RF (manufactured by ADEKA)

Example 8

The water-in-oil emulsified sunscreen cosmetic of Example 8 was produced by a usual method in accordance with the formula shown in Table 3, and the above measurements and evaluations were carried out. The results are shown in Table 3. The water-in-oil emulsified sunscreen cosmetic of Example 8 had a silky pleasant use impression.

TABLE 3

| | Components (mass %) | Example 8 |
|---|---|---|
| (A1) | Aluminum stearate-coated titanium dioxide *1 | 10.0 |
| (A2) | Silicone-coated zinc oxide *2 | 19.0 |
| (D) | Non-volatile dimethylpolysiloxane *4 | 1.5 |
| (C) | Liquid isoparaffin *5 | 7.0 |
| | Squalane *6 | 3.5 |
| (H) | Polyoxyethylene□methylpolysiloxane copolymer *7 | 1.5 |
| | Polyoxyethylene□methylpolysiloxane copolymer *8 | 1.4 |
| (J) | Dextrin palmitate *9 | 0.2 |
| (I) | Silicone-coated talc *10 | 4.0 |
| (F) | Neopentyl glycol di(2-ethylhexanoate) *11 | 1.5 |
| | Neopentyl glycol dicaprate *12 | 3.0 |
| (G) | Light liquid isoparaffin *13 | 5.0 |
| | Methylcyclopolysiloxane *16 | 29.8 |
| (B) | Dipropylene glycol *15 | 5.0 |
| (E) | Water | 7.6 |
| Total (mass %) | | 100.0 |
| Component (A1) content | | 10.0 |
| Component (A2) content | | 19.0 |
| Component (B) content | | 5.0 |
| Component (C) content | | 10.5 |
| Component (D) content | | 1.5 |
| Mass ratio [(B)/((A1) + (A2))] | | 0.17 |

TABLE 3-continued

| Components (mass %) | | Example 8 |
|---|---|---|
| Mass ratio [(C)/((A1) + (A2))] | | 0.36 |
| Mass ratio [(D)/((A1) + (A2))] | | 0.05 |
| Mass ratio [(D)/(C)] | | 0.14 |
| UV protect on effect (SPF) | Measured value | 91 |
| | Evaluation | 68 |
| | Measured value (%) | AA |
| Anti-adherence effect on air hazardous | Evaluation | AA |
| substance | | 68 |
| Absence of powdery feel | | AA |

In the table, *16 refers to Silicone TSF405A (manufactured by Momentive Performance Materials Japan LLC), and the other symbols have the same meanings as above.

REFERENCE SIGNS LIST

1: Sample for evaluation
2: Support plate
3: Mesh screen sieve
4: Air hazardous substance for evaluation
5: Air blower

The invention claimed is:

1. A water-in-oil emulsified sunscreen cosmetic comprising the following components (A1), (A2), (B), (C), (D), and (J):

(A1) 5 mass % or more of a hydrophobized titanium dioxide fine particle;
(A2) 10 mass % or more of a hydrophobized zinc oxide fine particle;
(B) a divalent polyol;
(C) from 2 mass % to 14 mass % of a non-volatile hydrocarbon oil;
(D) from 0.1 mass % to 3 mass % in total of at least one non-volatile silicone oil selected from the group consisting of dimethylpolysiloxane, methyl phenyl polysiloxane, methyl hydrogen polysiloxane, and tetramethyltetrahydrogenpolysiloxane; and
(J) from 0.2 to 5 mass % of a dextrin fatty acid ester,
wherein each mass % is with respect to 100 mass % of the water-in-oil emulsified sunscreen cosmetic,
wherein the mass ratio of the component (D) to the component (C), [(D)/(C)], is from 0.05 to 0.14, and
wherein the water-in-oil emulsified sunscreen cosmetic does not comprise a non-volatile silicone oil other than component (D).

2. The water-in-oil emulsified sunscreen cosmetic according to claim 1, wherein the mass ratio of the component (B) to the total of the components (A1) and (A2), [(B)/((A1)+(A2))], is from 0.05 to 0.75.

3. The water-in-oil emulsified sunscreen cosmetic according to claim 1, wherein the mass ratio of the component (C) to the total of the components (A1) and (A2), [(C)/((A1)+(A2))], is from 0.05 to 1.5.

4. The water-in-oil emulsified sunscreen cosmetic according to claim 1, wherein the mass ratio of the component (D) to the total of the components (A1) and (A2), [(D)/((A1)+(A2))], is from 0.005 to 0.2.

5. The water-in-oil emulsified sunscreen cosmetic according to claim 1, wherein the mass ratio of the component (D) to the total of the components (A1) and (A2), [(D)/((A1)+(A2))], is from 0.005 to 0.1.

6. The water-in-oil emulsified sunscreen cosmetic according to claim 1, wherein hydrophobization treatment of the component (A2) is selected from the group consisting of silicone treatment, alkylalkoxysilane treatment, fatty acid treatment, treatment with a fluorine-containing compound, treatment with an amino acid, and alkyl phosphate ester treatment.

7. The water-in-oil emulsified sunscreen cosmetic according to claim 1, wherein the content of the component (B) is from 1 mass % to 14 mass % with respect to 100 mass % of the water-in-oil emulsified sunscreen cosmetic.

8. The water-in-oil emulsified sunscreen cosmetic according to claim 1, wherein the content of the component (C) is from 6 mass % to 12 mass % with respect to 100 mass % of the water-in-oil emulsified sunscreen cosmetic.

9. The water-in-oil emulsified sunscreen cosmetic according to claim 1, further comprising:
from 0 mass % to 0.075 mass % of a coat-forming agent with respect to 100 mass % of the water-in-oil emulsified sunscreen cosmetic.

10. The water-in-oil emulsified sunscreen cosmetic according to claim 1, wherein a content of an ultraviolet absorber is 0 mass % with respect to 100 mass % of the water-in-oil emulsified sunscreen cosmetic.

11. The water-in-oil emulsified sunscreen cosmetic according to claim 1, wherein the component (C) non-volatile hydrocarbon oil is one or more selected from the group consisting of liquid isoparaffin and squalane.

12. A water-in-oil emulsified sunscreen cosmetic comprising the following components (A1), (A2), (B), (C), (D), and (J):

(A1) 5 mass % or more of a hydrophobized titanium dioxide fine particle;
(A2) 10 mass % or more of a hydrophobized zinc oxide fine particle;
(B) a divalent polyol;
(C) from 2 mass % to 14 mass % of a non-volatile hydrocarbon oil;
(D) from 0.1 mass % to 3 mass % of a non-volatile silicone oil; and
(J) from 0.2 to 5 mass % of a dextrin fatty acid ester,
wherein a content of an ultraviolet absorber is 0 mass %,
wherein each mass % is with respect to 100 mass % of the water-in-oil emulsified sunscreen cosmetic, and
wherein the water-in-oil emulsified sunscreen cosmetic does not comprise a polyether-modified silicone.

13. The water-in-oil emulsified sunscreen cosmetic according to claim 1, wherein the dextrin fatty acid ester is at least one selected from the group consisting of dextrin myristate, and dextrin (palmitate/hexyldecanoate).

14. The water-in-oil emulsified sunscreen cosmetic according to claim 12, wherein the dextrin fatty acid ester is at least one selected from the group consisting of dextrin myristate and dextrin (palmitate/hexyldecanoate).

15. The water-in-oil emulsified sunscreen cosmetic of claim 13, wherein the content of the dextrin fatty acid ester is from 3 to 5 mass % with respect to 100 mass % of the water-in-oil emulsified sunscreen cosmetic.

16. The water-in-oil emulsified sunscreen cosmetic of claim 14, wherein the content of the dextrin fatty acid ester is from 3 to 5 mass % with respect to 100 mass % of the water-in-oil emulsified sunscreen cosmetic.

17. The water-in-oil emulsified sunscreen cosmetic according to claim 1, wherein the component (C) non-volatile hydrocarbon oil comprises liquid isoparaffin and squalane at a combined content in a range of from 6 to 14 mass % with respect to 100 mass % of the water-in-oil emulsified sunscreen cosmetic.

18. The water-in-oil emulsified sunscreen cosmetic according to claim 17, wherein the component (C) has a combined content in a range of from 10.5 to 14 mass % with respect to 100 mass % of the water-in-oil emulsified sunscreen cosmetic.

19. The water-in-oil emulsified sunscreen cosmetic according to claim 12, wherein the component (C) non-volatile hydrocarbon oil comprises liquid isoparaffin and squalane at a combined content in a range of from 6 to 14 mass % with respect to 100 mass % of the water-in-oil emulsified sunscreen cosmetic.

* * * * *